United States Patent [19]

Cognacq

[11] 3,989,722
[45] Nov. 2, 1976

[54] 1-AMINOMETHYL-2,2-DIARYL-CYCLOPROPANE CARBOXAMIDES

[75] Inventor: Jean-Claude Cognacq, Garches, France

[73] Assignee: Societe Anonyme dite: Hexachimie, Rueil-Malmaison, France

[22] Filed: Nov. 19, 1973

[21] Appl. No.: 417,129

[30] Foreign Application Priority Data

Nov. 30, 1972 United Kingdom.............. 55276/72

[52] U.S. Cl..................... 260/343.7; 260/239 BF; 260/243 B; 260/247.2 A; 260/247.7 Z; 260/268 R; 260/268 CN; 260/293.76; 260/326.43; 260/326.5 M; 260/326.62; 260/326.85; 260/465 E; 260/501.1; 260/501.15; 260/501.17; 260/501.18; 260/501.19; 260/501.21; 260/558 A; 260/559 A; 424/244; 424/246; 424/248; 424/250; 424/267; 424/274; 424/304; 424/324; 260/293.75

[51] Int. Cl.²............. C07C 101/12; C07C 101/14; C07C 101/16; C07D 307/62

[58] Field of Search........ 260/557 R, 558 A, 559 A, 260/343.7, 501.1, 501.11, 501.15, 501.17, 501.19, 501.21, 501.18

[56] References Cited

UNITED STATES PATENTS

| | | | |
|---|---|---|---|
| 3,098,076 | 7/1963 | Baltzly et al. ................ | 260/570.9 X |
| 3,419,604 | 12/1968 | Kaiser et al. .......... | 260/570.5 CA X |
| 3,562,276 | 2/1971 | Teotino et al. ................ | 260/558 A |
| 3,574,742 | 4/1971 | Lapidus et al. ................ | 260/557 R |
| 3,646,146 | 2/1972 | Teotino et al. ............... | 260/557 R X |

OTHER PUBLICATIONS

"Cyclopropanes . . . ," Walborksy et al., CA 50:8472i (1956).
"Esters of 2,2-diphenylcyclopropanecarboxylic acids," Cognac CA 79:18432h (1973).

*The Chemistry of Amides*, Zabicky, ed., Interscience (1970), pp. 119, 525.

*Primary Examiner*—Robert V. Hines
*Assistant Examiner*—Thomas A. Waltz
*Attorney, Agent, or Firm*—Bacon & Thomas

[57] ABSTRACT

The invention relates to 1-aminomethyl-2,2-diaryl cyclopropane carboxamides of the general formula

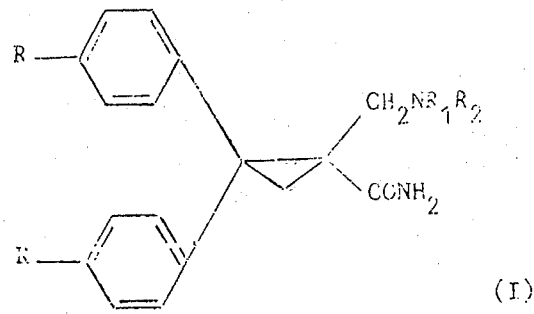

(I)

in which R represents the hydrogen atom, a halogen atom or a lower alkyl group or a lower alkoxy group; $R_1$ and $R_2$ which may be the same or different each represent a hydrogen atom, a lower alkyl group, an aryl group or an aralkyl group, in addition to which $R_1$ and $R_2$ together can form with the nitrogen atom to which they are attached a heterocyclic group with 5 to 7 peaks capable of containing a second hetero atom and capable of being substituted, and to their addition salts as new industrial products.

These products are suitable for therapeutic application, in particular in the treatment of Parkinson's disease.

9 Claims, No Drawings

1-AMINOMETHYL-2,2-DIARYL-CYCLOPROPANE CARBOXAMIDES

This invention relates to new derivatives of the 1-aminomethyl-2,2-diarylcyclopropane carboxamide type and to their addition salts as new industrial products. The invention also relates to a process for preparing these derivatives and to their therapeutic application.

The invention further relates to the new intermediate compounds for the synthesis of 1-aminomethyl-2,2-diarylcyclopropane carboxamides.

The new compounds according to the invention are selected from the group comprising:

a. 1-aminomethyl-2,2-diarylcyclopropane carboxamides corresponding to the general formula

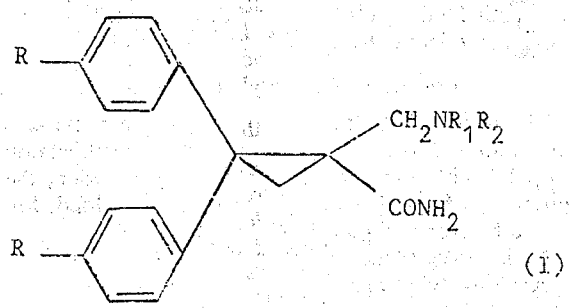

in which R represents the hydrogen atom, a halogen atom or a lower alkyl group or a lower alkoxy group, $R_1$ and $R_2$ which may be the same or different each represent the hydrogen atom, a lower alkyl group, an aryl group or an aralkyl group, in addition to which $R_1$ and $R_2$ together can form with the nitrogen atom to which they are attached a heterocyclic group with 5 to 7 peaks capable of containing a second hetero atom and capable of being substituted; and b. their addition salts.

In the context of the invention, halogen atoms are fluorine, chlorine, bromine and iodine atoms, the preferred halogens being fluorine, chlorine and bromine. A lower alkyl group is a linear or branched hydrocarbon chain with 1 to 5 carbon atoms.

According to the invention, the preferred aralkyl group is the benzyl group.

The N-heterocyclic groups $NR_1R_2$ can contain a second hetero atom such as, in particular, O, S and N. They can also be substituted by lower alkyl or lower hydroxyalkyl groups. The heterocyclic groups $NR_1R_2$ include in particular the pyrrolidine, morpholine, thiomorpholine, 3,5-dimethylmorpholine, piperidine, 4-methylpiperidine, piperazine, 4-methylpiperazine, 4-β-hydroxyethylpiperazine and azepine groups.

Addition salts in the context of the invention are acid addition salts and ammonium salts. The acid addition salts are obtained from the free base by methods known per se, in particular by reaction with a mineral or organic acid. Acids suitable for forming addition salts include in particular hydrochloric acid, sulphuric acid, acids of phosphorus, oxalic acid, succinic acid, methane sulphonic acid, cyclohexylsulphamic acid, formic acid, aspartic acid, glutamic acid, N-acetylaspartic acid, N-acetylglutamic acid, ascorbic acid, maleic acid, malic acid, fumaric acid, lactic acid, benzoic acid and cinnamic acid. The ammonium salts are obtained from the free base or from an acid addition salt. Among the ammonium salts, reference is made in particular to the iodomethylate.

The process by which compounds of formula I are prepared is distinguished by the fact that:

a. an ethylenic aminonitrile corresponding to the formula

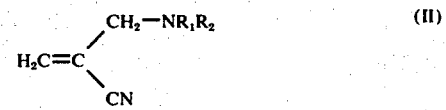

in which $R_1$ and $R_2$ are as defined above, is reacted, preferably in stoichiometric quantities, with a diaryldiazomethane corresponding to the formula the Escherichia

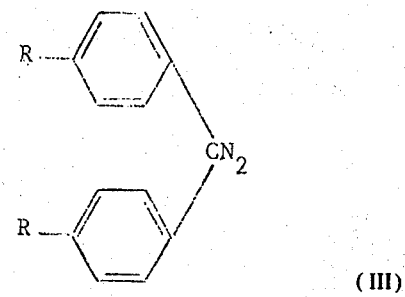

in which R is as defined above, in an inert solvent at the reflux temperature of that solvent, and b. the nitrile group in the product thus obtained which corresponds to the general formula

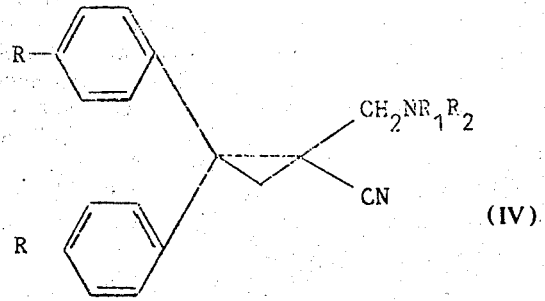

in which R, $R_1$ and $R_2$ are as defined above, is hydrolysed with hydrochloric acid to form an amide of formula I.

In one preferred embodiment of the process according to the invention, reaction a) is carried out in heptane or chloroform whilst reaction b) is carried out by reacting 0.2 mole of nitrile IV with 200 cc of concentrated hydrochloric acid ($d = 1.18$) for about 15 hours at a temperature of 50° C.

Reaction (b) can be carried out either with the nitrile IV or with an equivalent quantity of an acid addition salt of that nitrile, more especially the hydrochloride or the maleate.

The final amide of formula I is then isolated by a method known per se: alkalisation with sodium hydroxide, extraction with chloroform, drying over magnesium sulphate, elimination of the solvent and recrystallisation.

The new intermediates are the nitriles of formula IV and their acid addition salts, especially the hydrochloride and the maleate.

The aminonitriles of formula II are obtained by Mannich's reaction from cyanoacetic acid and the corresponding amine $HNR_1R_2$ in the presence of dioxan as solvent, cf. Bull. Soc. Chim, (1971), No. 11, pages 4160 et seq.

The compounds of formula I and their non-toxic addition salts can be used for therapeutic purposes, in particular as anti-cholinergic, anti-spasmodic and/or anti-Parkinsonian agents.

Therapeutic compositions suitable for use in accordance with the invention contain a pharmaceutically effective quantity of at least one compound of formula I or one of its non-toxic addition salts in association with a physiologically acceptable excipient.

The invention is illustrated by the following Examples.

Examples 1 to 3 relate to the production of aminonitriles of formula II which are original.

EXAMPLE 1

2-(N-Methylpiperazinomethyl)-acrylonitrile percent

Formula II; $NR_1R_2 =$

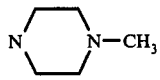

0.5 Mole of N-methylpiperazine are added to 0.5 mole of cyanoacetic acid in 150 cc. of dioxan at a temperature kept at around 0° C. This is followed by the addition of 1 mole of formaldehyde in the form of a 30% aqueous solution. After the heat effect has abated, the mixture is stirred until there is no further evolution of carbon dioxide gas (approximately 2 hours). 200 cc. of water are then added, the product extracted with ether, dried over sodium sulphate and the ether removed in vacuo, followed by distillation.

Yield: 81%. B.p. (11 mm Hg): 120°–123° C
Analysis: N% Calculated 25.4, Found 25.47.

EXAMPLE 2

2-Azepinomethylacrylonitrile

Formula II; $NR_1R_2 =$ azepine

The procedure is as in Example 1, except that the N-methylpiperazine is replaced by azepine (0.5 mole).
Yield: 83%. B.p. (15 mm Hg): 115°–120° C
Analysis: N% Calculated 17.08, Found 16.96.

EXAMPLE 3

2-(N-Methylbenzylaminomethyl)-acrylonitrile

Formula II; $NR_1R_2 = N(CH_3)CH_2C_6H_5$

The procedure is as in Example 1, except that the N-methylpiperazine is replaced by N-methylbenzylamine.
Yield: 79%. B.p. (0.1 mm Hg): 110°–115° C.
Analysis: N% Calculated 15.05, Found 15.09.

Examples 4 to 13 relate to the production of nitriles of formula IV.

EXAMPLE 4

1-Dimethylaminomethyl-2,2-diphenylcyclopropane carbonitrile

Formula IV; R = H, $NR_1R_2 = N(CH_3)_2$ 0.4 Mole of 2-dimethylaminomethyl acrylonitrile II are added to 0.4 mole of diphenyldiazomethane III in 250 cc. of heptane and the mixture heated under reflux until it becomes colourless. This takes approximately 6 hours. The heptane is evaporated and the product taken up in petroleum ether. After crystallisation, the product is filtered, washed with pentane and dried.
Yield: 76%. M.p.: 98° C.
Analysis: N% Calculated 10.01, Found 10.19.

EXAMPLE 5

1-Diethylaminomethyl-2,2-diphenylcyclopropane carbonitrile

Formula IV; R = H, $NR_1R_2 = N(C_2H_5)_2$

The procedure is as in Example 4, except that the 2-dimethylaminomethyl acrylonitrile is replaced by 2-diethylaminomethyl acrylonitrile (0.4 mole).

Preparation of the hydrochloride

The residue left after evaporation of the heptane is taken up in 200 cc. of ether, followed by acidification to pH 1 with ethyl chloride. After crystallisation, the product is filtered, washed with ether and dried, followed by recrystallisation from isopropanol.
Yield: 75%. M.p.: 220° C.
Analysis: N% Calculated 8.22, Found 8.3.

EXAMPLE 6

1-Pyrrolidinomethyl-2,2-diphenylcyclopropane carbonitrile

Formula IV; R = H, $NR_1R_2 =$ pyrrolidine

The procedure is as in Example 4, except that the 2-dimethylaminomethyl acrylonitrile is replaced by 2-pyrrolidinomethyl acrylonitrile (0.4 mole).

Preparation of the maleate

The residue left following evaporation of the heptane is taken up in 0.4 mole of malic acid in 250 cc. of ethanol, followed by the addition of 250 cc. of ether. The product precipitates and is filtered, washed with ether and recrystallised from ethanol.
Yield: 71%. M.p.: 173° C.
Analysis: N% Calculated 6.7, Found 6.63.

EXAMPLE 7

1-Piperidinomethyl-2,2-diphenylcyclopropane carbonitrile

Formula IV; R = H, $NR_1R_2 =$ piperidine

The procedure is as in Example 4, except that the 2-dimethylaminomethyl acrylonitrile is replaced by 2-piperidinomethylacrylonitrile (0.4 mole).
Yield: 70%. M.p.: 121° C.
Analysis: N% Calculated 8.85, Found 8.7.

EXAMPLE 8

1-Morpholinomethyl-2,2-diphenylcyclopropane carbonitrile

Formula IV; R = H, $NR_1R_2 =$ morpholine

The procedure is as in Example 4, except that the 2-dimethylaminomethyl acrylonitrile is replaced by 2-morpholinomethyl acrylonitrile (0.4 mole). After evaporation of the heptane, the residue is crystallised in a mixture of ethyl acetate and petroleum ether (70:30).
Yield: 69%. M.p.: 144° C.
Analysis: N% Calculated 8.79, Found 8.83

EXAMPLE 9

1-(N-Methylbenzylaminomethyl)-2,2-diphenylcyclopropane carbonitrile

Formula IV; R = H, NR$_1$R$_2$ = N(CH$_3$)CH$_2$C$_6$H$_5$

The procedure is as in Example 4, except that the 2-dimethylaminomethyl acrylonitrile is replaced by 2-(N-methylbenzylaminomethyl)-acrylonitrile (0.4 mole) prepared in accordance with Example 3. spray-dried the disappearance of colour, the product crystallises from the reaction medium in the absence of heat, is filtered and then recrystallised from methylethylketone.

Yield: 70%. M.p.: 168° C.
Analysis: N% Calculated 7.95, Found 7.87.

EXAMPLE 10

1-(N-Methylpiperazinomethylethyl)-2,2-diphenylcyclopropane carbonitrile

Formula IV; R = H, NR$_1$R$_2$ =

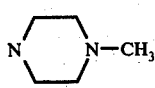

The procedure is as in Example 4, except that the 2-dimethylaminomethyl acrylonitrile is replaced by 2-(N-methylpiperazinomethyl)-acrylonitrile (0.4 mole) prepared in accordance with Example 1. Following evaporation of the heptane, the residue is crystallised in a mixture of ether and petroleum ether (70:30).

Yield: 69%. M.p. 118° C
Analysis: N% Calculated 12.7, Found 12.68

EXAMPLE 11

1-Azepinomethyl-2,2-diphenylcyclopropane carbonitrile

Formula IV; R = H, NR$_1$R$_2$ = azepine

The procedure is as in Example 4, except that the 2-dimethylaminomethyl acrylonitrile is replaced by 2-azepinomethyl acrylonitrile (0.4 mole) prepared in accordance with Example 2. The residue left following evaporation of the heptane is crystallised in a mixture of isopropyl acetate and pentane (70:30).

Yield: 67%. M.p.: 114° C.
Analysis: N% Calculated 8.48, Found 8.57

EXAMPLE 12

1-Dimethylaminomethyl-2,2-di-p-tolyl cyclopropane carbonitrile

Formula IV; R = CH$_3$, NR$_1$R$_2$ = N(CH$_3$)$_2$

The procedure is as in Example 4, except that 0.4 mole of di-p-tolyl diazomethane is reacted with 0.4 mole of 2-dimethylaminomethyl acrylonitrile in 250 cc. of chloroform. Following evaporation of the chloroform, the residue is taken up in 250 cc. of pentane. After crystallisation, the product group, filtered, washed with pentane and dried.

Yield: 65%. M.p.: 97° C.
Analysis: N% Calculated 9.2, Found 9.13

EXAMPLE 13

1-Piperidinomethyl-2,2-di-p-chlorophenyl cyclopropane carbonitrile

Formula IV; R = Cl, NR$_1$R$_2$ =

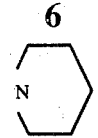

The procedure is as in Example 4, except that 0.4 mole of di-p-chlorophenyl diazomethane are reacted with 0.4 mole of 2-piperidinomethyl acrylonitrile in 250 cc. of chloroform.

Preparation of the hydrochloride

Following evaporation of the chloroform, the residue is taken up in 200 cc. of ethanol, followed by the addition of ethyl chloride up to pH 1 and then by the addition of 200 cc. of ether. After crystallisation, the product is filtered, washed with ether and recrystallised from 95% alcohol.

Yield: 63%. M.p. 245° C.
Analysis: N% Calculated 6.85, Found 7.0

Examples 14 to 23 relates to the amides of formula I.

EXAMPLE 14

1-Dimethylaminomethyl-2,2-diphenyl cyclopropane carboxamide

Formula I; R = H, NR$_1$R$_2$ = N(CH$_3$)$_2$

A mixture of 0.2 mole of nitrile IV prepared in accordance with Example 4 and 200 cc. of concentrated hydrochloric acid ($d = 1.18$) is heated at 50° C for 15 hours. The product is alkalised with sodium hydroxide, extracted with chloroform, dried over magnesium sulphate and the chloroform removed in vacuo. The residue is crystallised in a mixture of cyclohexane and petroleum ether (60:40).

Yield: 34%. M.p. 154°–155° tribromosalicylanilide
Analysis: N% Calculated 9.51, Found 9.42

EXAMPLE 15

1-Diethylaminomethyl-2,2-diphenylcyclopropane carboxamide

Formula I; R = H, NR$_1$R$_2$ = N(C$_2$H$_5$)$_2$

The procedure is as in Example 14, except that the 1-dimethylaminomethyl-2,2-diphenylcyclopropane carbonitrile is replaced by the hydrochloride of the product of Example 5 (0.2 mole).

Preparation of the methane sulphonate

Following evaporation of the chloroform, the residue is taken up in a mixture of ether and petroleum ether. After crystallisation, the product is filtered and dried. The crystals are taken up in 100 cc. of isopropanol, followed by the addition of 0.2 mole of methane sulphonic acid in 200 cc. of ether, and then be trituration. After crystallisation the product is filtered and recrystallised from a mixture of isopropanol and ether (70:30).

Yield: 31% M.p.: 208° C
Analysis: N% Calculated 6.7, Found 6.63.

Preparation of the iodomethylate 0.1 Mole of the preceding methane sulphonate is taken up in 110 cc. of 1N NaOH. The mixture is extracted with chloroform, dried over magnesium sulphate and the solvent removed in vacuo. The residue is taken up with 150 cc. of acetone, 0.12 mole of methyl iodide added to the resulting solution which is then left standing for 3 hours, followed by filtration, washing with acetone and drying.

Yield: 92%. M.p.: 260° C.

Analysis: N% Calculated 6.04, Found 6.10

The hydrochloride of the product of Example 15 was also prepared.

EXAMPLE 16

1-Pyrrolidinomethyl-2,2-diphenylcyclopropane carboxamide

Formula I; R = H, $NR_1R_2$ = pyrrolidine

The procedure is as in Example 14, except that the 1-dimethylaminomethyl-2,2-diphenylcyclopropane carbonitrile is replaced by the maleate of 1-pyrrolidinomethyl-2,2-diphenylcyclopropane carbonitrile (0.2 mole) prepared in accordance with Example 6. Following evaporation of the chloroform, the residue is taken up in ether. After precipitation, the product is filtered and dried, followed by recrystallisation from a mixture of chloroform and petroleum ether (65:35).

Yield: 37%. M.p.: 182° C.

Analysis: N% Calculated 8.75, Found 8.87

EXAMPLE 17

1-Piperidinomethyl-2,2-diphenylcyclopropane carboxamide

Formula I; R = H, $NR_1R_2$ =

The procedure is as in Example 14, except that the 1-dimethylaminomethyl-2,2-diphenylcyclopropane carbonitrile is replaced by 1-piperidinomethyl-2,2-diphenyl cyclopropane carbonitrile (0.2 mole) prepared in accordance with Example 7. Following evaporation of the chloroform, the product is taken up in ether. After crystallisation, the product is filtered and then recrystallised from a mixture of chloroform and petroleum ether (65:35).

Yield: 44%. M.p.: 215° C.

Analysis: N% Calculated 8.37, Found 8.40

EXAMPLE 18

1-Morpholinomethyl-2,2-diphenylcyclopropane carboxamide

Formula I; R = H, $NR_1R_2$ =

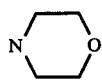

The procedure is as in Example 14, except that the 1-dimethylaminomethyl-2,2-diphenylcyclopropane carbonitrile is replaced by 1-morpholinomethyl-2,2-diphenylcyclopropane carbonitrile (0.2 mole) prepared in accordance with Example 8. Following evaporation of the chloroform, the residue is taken up in ether. After precipitation, the product is filtered and recrystallised from a mixture of chloroform and petroleum ether (70:30).

Yield: 57%. M.p.: 216° C.

Analysis: N% Calculated 8.33, Found 8.21.

EXAMPLE 19

1-(N-Methylbenzylaminomethyl)-2,2-diphenylcyclopropane carboxamide

Formula I; R = H, $NR_1R_2 = N(CH_3)CH_2C_6H_5$

The procedure is as in Example 14, except that the 1-dimethylaminomethyl-2,2-diphenylcyclopropane carbonitrile is replaced by 1-(N-methylbenzylaminomethyl)-2,2-diphenyl cyclopropane carbonitrile (0.2 mole) prepared in accordance with Example 9. Following evaporation of the chloroform, the residue is recrystallised from ethyl acetate.

Yield: 49%. M.p.: 160° C

Analysis: N% Calculated 7.56, Found 7.49

EXAMPLE 20

1-(N-Methylpiperazinomethyl)-2,2-diphenylcyclopropane carboxamide

Formula I; R = H, $NR_1R_2$ =

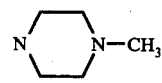

The procedure is as in Example 14, except that the 1-dimethylaminomethyl-2,2-diphenylcyclopropane carbonitrile is replaced by 1-(N-methylpiperazinomethyl)-2,2-diphenyl cyclopropane carbonitrile (0.2 mole) prepared in accordance with Example 10. After evaporation of the chloroform, the residue is taken up in ether. After crystallisation, the product is filtered and recrystallised from ethanol.

Yield: 38%. M.p.: 226° C.

Analysis: N% Calculated 12.01, Found 12.17

EXAMPLE 21

1-Azepinomethyl-2,2-diphenylcyclopropane carboxamide

Formula I; R = H, $NR_1R_2$ = azepine

The procedure is as in Example 14, except that the 1-dimethylaminomethyl-2,2-diphenylcyclopropane carbonitrile is replaced by 1-azepinomethyl-2,2-diphenylcyclopropane carbonitrile (0.2 mole) prepared in accordance with Example 11. After evaporation of the chloroform, the residue is taken up in ether. After crystallisation, the product is filtered and recrystallised from a mixture of chloroform and petroleum ether (60:40).

Yield: 39%. M.p.: 146° C

Analysis: N% Calculated 8.05, Found 7.98.

EXAMPLE 22

1-Dimethylaminomethyl-2,2-di-p-tolylcyclopropane carboxamide

Formula I; R = $CH_3$, $NR_1R_2 = N(CH_3)_2$

The procedure is as in Example 14, except that the 1-dimethylaminomethyl-2,2-diphenylcyclopropane carbonitrile is replaced by 1-dimethylaminomethyl-2,2-di-p-tolyl cyclopropane carbonitrile (0.2 mole) prepared in accordance with Example 12.

Preparation of the maleate

After evaporation of the chloroform, the residue is taken up in ether. After crystallisation, the product is filtered and dried. The residue is taken up in a boiling solution of 0.2 mole of maleic acid in 150 cc. of isopropanol, followed by the addition of 200 cc. of ether. After precipitation, the product is filtered and recrystallised from 95% isopropanol.

Yield: 41%. M.p.: 203° C.

Analysis: N% Calculated 6.39, Found 6.27

EXAMPLE 23

1-Piperidinomethyl-2,2-di-p-chlorophenyl cyclopropane carboxamide

Formula I; R = Cl, $N_1R_2$ =

The procedure is as in Example 14, except that the 1-dimethylaminomethyl-2,2-diphenyl cyclopropane carbonitrile is replaced by the hydrochloride of 1-piperidinomethyl-2,2-di-p-chlorophenylcyclopropane carbonitrile (0.2 mole) prepared in accordance with Example 13. After evaporation of the chloroform, the residue is taken up in ether. After crystallisation, the product is filtered and recrystallised from a mixture of chloroform and petroleum ether (70:30).

Yield: 28%. M.p. 211° C

Analysis: N% Calculated 6.95, Found 7.03

The results of pharmacological tests carried out with the products of formula I according to the invention are summarised in the following. Unless mentioned otherwise, the products were studied in the form of free bases.

1. Acute Toxicity

The products to be tested are administered intraperitoneally to groups of two mice (S) and two rats (R) of the SPF-type. Mortality is recorded seven days after the treatment.

Table I below shows the lethal dose 0 (DL 0) and the lethal dose 100 (DL 100) of the products of Examples 14 to 23.

2. Oxotremorine-Induced Antagonism

The products to be tested are administered intraperitoneally to batches of 6 SPF mice weighing from 18 to 22 g, followed 30 minutes afterwards by the intraperitoneal administration of 0.5 mg/kg of oxotremorine. Recordings are then taken . either of the rectal temperature by thermocouple, . or of the degree of inhibition of trembling, salivation, lacrimation by arbitrarily marking the intensity of the phenomenon with scores of 0 to 3.

Tables II and III below show the percentage inhibition of hypothermia and trembling in relation to control animals which had only received oxotremorine.

Tables III bis to III ter below relate to the percentage inhibition of salivation and lacrimation by the hydrochloride and iodomethylate of the product of Example 15.

3. Acetylcholine-Induced Antagonism In the isolated ileum of guinea pigs

Part of the isolated ileum of a guinea pig is kept alive in aerated Tyrode's solution kept at 37° C. A contraction is induced by the addition to the bath of a solution of acetylcholine in such a quantity that the concentration in the bath amounts to 0.02 γ/ml.

Inhibition of the contraction after preliminary contact with a solution of the products to be tested is then measured.

Table IV below shows the percentage inhibition in dependence upon the concentrations of product in the bath.

Acetylcholine aerosol

The products to be tested are intraperitoneally administered to guinea pigs weighing from 350 to 500 g 30 minutes before exposure in a chamber to an acetylcholine aerosol for at most 5 minutes. The number of animals which undergo bronchiospasm is then counted. Table V below shows the percentage inhibition levels in dependence upon the doses administered.

4. Anti-Cataleptic Activity 12.5 mg/kg of prochlorperazine are administered intraperitoneally to batches of 6 rats. The products to be tested are administered intraperitoneally 2 hours after the prochlorperazine. The catalepsy is marked + or − in accordance with BOISSIER and SIMON. The scores of the four tests are totalled. The results are set out in Table VI below.

The activities summarised in the foregoing show that the products according to the invention are suitable for use in the treatment of Parkinson's disease, in the treatment of extrapyramidal disorders caused by neuroleptics (this is the case in particular with the product of Example 14) and in the treatment of spasms affecting the unstriped musculature (this is the case in particular with the product of Example 15).

Quarternisation of the product of Example 15 with methyl iodide results in the formation of a product which suppresses central activity and increases peripheral activity.

Clinical tests have confirmed these indications because good results have been obtained in the treatment of spasms and Parkinson's disease in humans by administering the products of formula I or their addition salts in the form of capsules, tablets or dragees containing 2 mg of active principle, suppositories containing 10 mg of active principle and injectable ampoules containing 1 mg of active principle, the daily dose administered to adults being from 5 to 20 mg of active principle.

Some of the clinical tests carried out are summarised in the following.

The administration of capsules containing 2 mg of the product of Example 16 in a daily dose of 3 to 6 capsules each containing 2 mg of active principle either alone or in association with 1-dopa enables Parkinson's syndrome to be corrected. Associated with neuroleptics, the product of Example 16, in the same doses as above, enables iatrogenic catatonic rigidity to be completely eliminated.

Finally, the product of Example 15 administered in the form of capsules containing 2 mg of active principle or ampoules containing 0.5 mg of active principle suppresses spasms affecting the digestive, genito-urinary and biliary unstriped musculature.

The iodomethylate of the product of Example 15 is twice as active as the hydrochloride on the one hand and does not have any effect on the central nervous system on the other hand. Its use as an antispasmodic makes it an interesting product because it has few side effects.

TABLE I

| Examples | | 14 | 15 | 16 | 17 | 18 | 19 | 20 | 21 | 22 | 23 |
|---|---|---|---|---|---|---|---|---|---|---|---|
| $DL_0$ | R | 64 | 128 | 128 | >1024 | >512 | >512 | 64 | 256 | 128 | >512 |
|  | S | 128 | 128 | 64 | >1024 | >512 | >512 | 256 | 256 | 256 | >512 |
| $DL_{100}$ | R | 512 | 256 | 256 | >1024 | >512 | >512 | >256 | 512 | 256 | >512 |
|  | S | 256 | 256 | 256 | >1024 | >512 | >512 | 512 | >512 | 512 | >512 |

TABLE II (hypothermia)

| Dose mg/kg I.P. Examples | 14 | 15 | 16 | 17 | 18 | 19 | 20 | 21 | 22 | 23 |
|---|---|---|---|---|---|---|---|---|---|---|
| 1 | — | — | — | — | — | — | — | — | — | — |
| 2 | 32 | 29 | — | — | — | — | — | — | — | — |
| 4 | 47 | 40 | — | — | — | — | — | — | — | — |
| 8 | 46 | 41 | — | — | — | — | — | — | — | — |
| 16 | 65 | 66 | — | 32 | — | — | — | — | — | — |
| 32 | 73 | 86 | 26 | 26 | — | 25 | 38 | 6 | — | — |
| 64 | — | — | 72 | 53 | — | 39 | 47 | 4 | 4 | 24 |
| 128 | — | — | — | 74 | 60 | 52 | 68 | — | 5 | 43 |
| 256 | — | — | — | — | 100 | 83 | — | — | — | 61 |
| 512 | — | — | — | — | — | 95 | — | — | — | — |

TABLE III (trembling)

| Dose mg/kg I.P. Examples | 14 | 15 | 16 | 17 | 18 | 19 | 20 | 21 | 22 | 23 |
|---|---|---|---|---|---|---|---|---|---|---|
| 0,25 | 36 | — | — | — | — | — | — | — | — | — |
| 0,50 | — | — | — | — | — | — | — | — | — | — |
| 1 | 28 | 41 | — | — | — | — | — | — | — | — |
| 2 | 30 | 65 | — | — | — | — | — | — | — | — |
| 4 | 62 | 85 | — | 26 | — | — | — | — | — | — |
| 8 | 90 | — | — | 28 | — | — | — | — | — | — |
| 16 | 100 | — | 36 | 42 | — | 41 | — | 7 | — | 41 |
| 32 | — | — | — | 49 | — | — | 22 | 37 | 15 | — |
| 64 | — | — | 58 | 75 | — | 68 | — | 64 | 35 | 64 |
| 128 | — | — | — | 97 | 39 | — | 22 | — | 71 | — |
| 256 | — | — | — | — | 70 | — | — | — | — | — |

TABLE III bis (salivation)

| Dose mg/kg oral | Example 15 Hydrochloride | Example 15 Iodomethylate |
|---|---|---|
| 4 | 7 | — |
| 8 | 84 | 15 |
| 16 | 97 | — |
| 32 | 100 | 47 |
| 64 | — | — |
| 128 | — | 100 |

TABLE III ter (lacrimation)

| Dose mg/kg oral | Example 15 Hydrochloride | Example 15 Iodomethylate |
|---|---|---|
| 4 | 24 | — |
| 8 | 79 | 5 |
| 16 | 100 | — |
| 32 | — | 70 |
| 64 | — | — |
| 128 | — | 100 |

TABLE IV

| Dose γ/ml | Examples 14 | 15 HCl | 15 $ICH_3$ | 16 | 17 | 18 | 20 | 22 | 23 |
|---|---|---|---|---|---|---|---|---|---|
| 0,0005 | 3 | — | — | — | 28 | — | — | — | 8 |
| 0,002 | 9 | 16 | 19 | — | 41 | — | — | — | 27 |
| 0,005 | 30 | 20 | 43 | — | 74 | — | — | — | 31 |
| 0,02 | 82 | 83 | 90 | 7 | 94 | — | — | — | 44 |
| 0,05 | 98 | 92 | — | 49 | — | 45 | 0 | 37 | 61 |
| 0,2 | — | — | — | 90 | — | — | — | — | 100 |
| 0,5 | — | — | — | 98 | — | — | — | — | — |
| 2 | — | — | — | — | — | 68 | 96 | 100 | — |

TABLE V

| Dose mg/kg I.P. | Examples | 14 | 15 HCl | 15 ICH₃ | 16 | 17 | 18 | 21 | 22 |
|---|---|---|---|---|---|---|---|---|---|
| 0,5 | | — | — | — | 0 | — | — | — | — |
| 1 | | — | — | 17 | 25 | — | — | — | — |
| 2 | | 16 | 16 | 50 | 58 | 16 | — | — | — |
| 4 | | 50 | 50 | 67 | 91 | 50 | — | — | — |
| 8 | | 66 | 83 | 84 | — | 66 | 0 | 0 | 17 |
| 16 | | 100 | 100 | 100 | — | 100 | 0 | 33 | 33 |
| 32 | | — | — | — | — | — | 17 | 66 | 50 |
| 64 | | — | — | — | — | — | 50 | — | 67 |
| 128 | | — | — | — | — | — | 83 | — | — |

TABLE VI

| Dose mg/kg I.P. | Examples | 14 | 15 | 16 | 17 | 18 | 19 | 20 | 21 | 22 | 23 |
|---|---|---|---|---|---|---|---|---|---|---|---|
| 0,5 | | — | — | — | — | — | — | — | — | — | — |
| 1 | | — | — | — | — | — | — | — | — | — | — |
| 2 | | 22 | — | — | — | — | — | — | — | — | — |
| 4 | | 76 | — | — | — | — | — | — | — | — | — |
| 8 | | 93 | 62 | 21 | — | — | — | — | — | — | — |
| 16 | | 100 | 61 | 74 | — | — | — | — | — | — | — |
| 32 | | — | 98 | 80 | — | — | — | — | 48 | — | — |
| 64 | | — | 100 | 100 | — | — | — | 5 | 89 | 28 | — |
| 128 | | — | — | — | — | — | — | 21 | — | 100 | — |
| 256 | | — | — | — | 95 | 76 | 47 | — | — | — | 50 |
| 512 | | — | — | — | 98 | 63 | 45 | — | — | — | 63 |

I claim:
1. Compounds selected from the group consisting of:
   a. 1-aminomethyl-2,2-diarylcyclopropane carboxamides corresponding to the general formula (I)

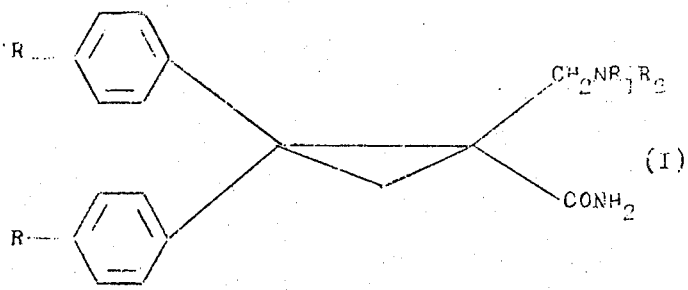

in which R represents the hydrogen atom, a halogen atom or a lower alkyl or lower alkoxy group; $R_1$ and $R_2$ which may be the same or different each represent the hydrogen atom, a lower alkyl group, phenyl or benzyl; and
   b. their non-toxic acid addition salts and quaternary ammonium salts.

2. Compounds according to claim 1 wherein $R_1$ and $R_2$ which may be the same or different each represent the hydrogen atom, a lower alkyl group, or a benzyl group.

3. Compounds according to claim 1, wherein $R_1$ and $R_2$ which may be the same or different each represent a hydrogen atom, or a lower alkyl group.

4. Compounds according to claim 1, wherein R is H, $ch_3$, or Cl.

5. Compounds according to claim 1, wherein $NR_1R_2$ is $N(CH_3) CH_2 C_6H_5$.

6. 1-dimethylaminomethyl-2,2-diphenylcyclopropane carboxamide and its addition salts.

7. 1-diethylaminomethyl-2,2-diphenylcyclopropane carboxamide and its addition salts.

8. 1-dimethylaminomethyl-2,2-di-p-tolylcyclopropane carboxamide and its addition salts.

9. Compounds according to claim 1 wherein the acid addition salt and quaternary ammonium salts are formed from the following, hydrochloric acid, sulphuric acid, phosphorus acid, oxalic acid, succinic acid, methane sulphonic acid, cyclohexylsulphamic acid, formic acid, aspartic acid, glutamic acid, N-acetylaspartic acid, N-acetylglutamic acid, ascorbic acid, maleic acid, malic acid, fumaric acid, lactic acid, benzoic acid, and the quaternary ammonium salt is the iodomethylate.

* * * * *